United States Patent [19]
Dair et al.

[11] Patent Number: 6,001,082
[45] Date of Patent: Dec. 14, 1999

[54] MEDICATION DELIVERY PEN WITH AN INTEGRAL MAGNIFYING POCKET CLIP

[75] Inventors: Thomas M. Dair, Yorktown Heights; Maximillian Philip Burton, New York; Marco Carroll Perry, Brooklyn, all of N.Y.; David P. Farrage, Weehawken, N.J.

[73] Assignee: Becton Dickinson and Company, Franklin Lakes, N.J.

[21] Appl. No.: 09/026,937

[22] Filed: Feb. 20, 1998

[51] Int. Cl.⁶ .................................................. A61M 5/00
[52] U.S. Cl. ........................................ 604/207; 604/187
[58] Field of Search ........................... 604/207–211, 181, 604/187

[56] References Cited

U.S. PATENT DOCUMENTS

| | | |
|---|---|---|
| 2,586,581 | 2/1952 | Tschischeck . |
| 4,743,234 | 5/1988 | Leopoldi et al. ...................... 604/187 |
| 5,295,976 | 3/1994 | Harris ...................................... 604/211 |
| 5,468,233 | 11/1995 | Schraga ................................. 604/207 |
| 5,498,243 | 3/1996 | Vallelunga et al. ................... 604/197 |
| 5,545,147 | 8/1996 | Harris ...................................... 604/209 |

*Primary Examiner*—Corrine McDermott
*Attorney, Agent, or Firm*—Alan W. Fiedler

[57] ABSTRACT

A medication delivery pen having a magnifier for sufficiently magnify dosage numerals used by the user to set the desired dose of medication to be dispensed by the medication delivery pen. The magnifier being integral with a pocket clip on the medication delivery pen, such that the magnifier means extends over a window through which the user sees the set desired dose and at a predetermined distance such that the dose is sufficiently magnified for the user.

7 Claims, 5 Drawing Sheets

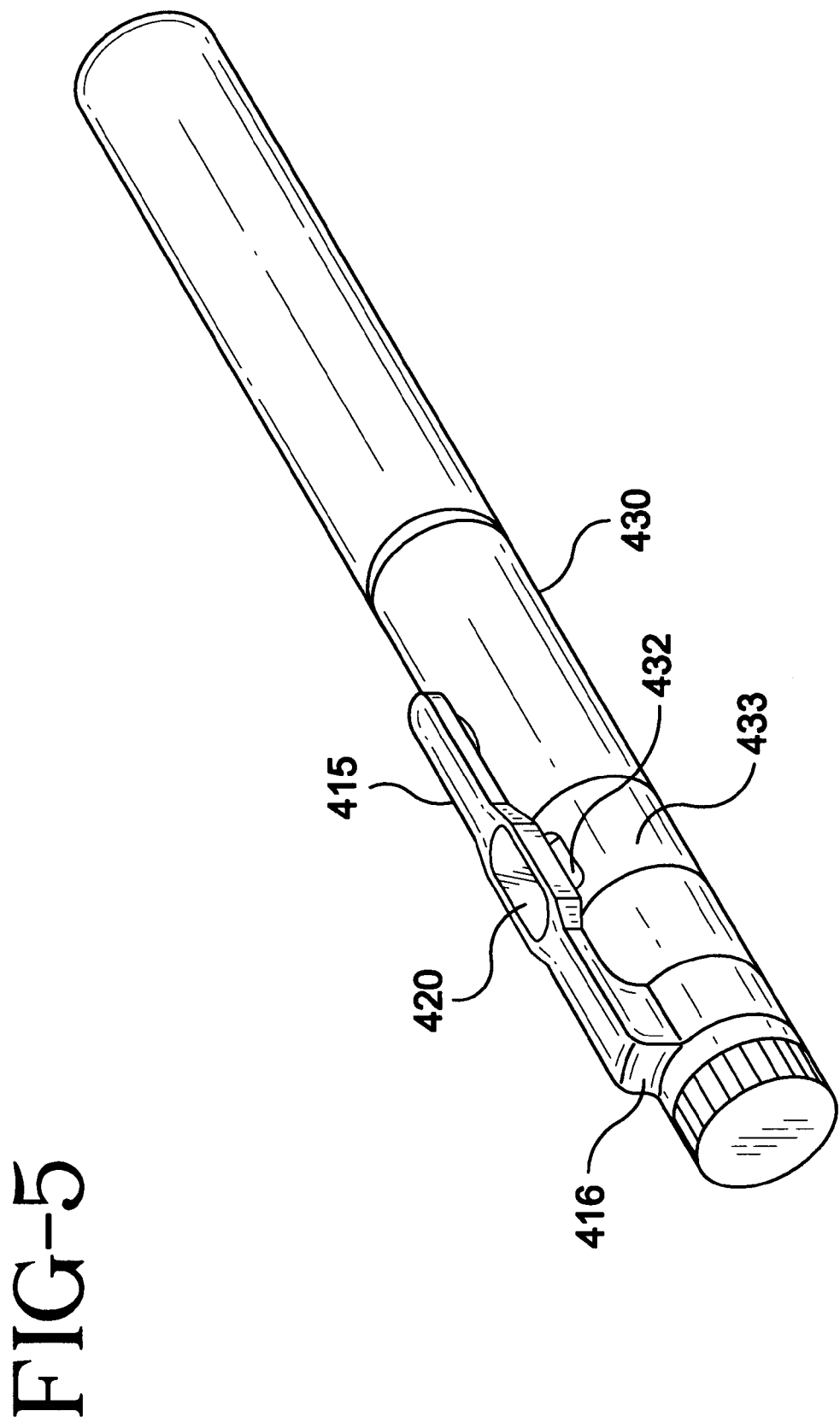

MEDICATION DELIVERY PEN WITH AN INTEGRAL MAGNIFYING POCKET CLIP

BACKGROUND OF THE INVENTION

1. Field of the Invention

The present invention relates to medication delivery pens having integral means for magnifying dosage numerals representing the dose being set by a user and, more specifically, a medication delivery pen having an integral magnifying pocket clip for magnifying the dosage numerals on the pen.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula may be mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastomeric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for designating a dose of medication to be delivered by the pen and a driving apparatus for urging the plunger of the vial distally for a distance corresponding to the selected dose.

The user of the pen mounts a prior art double-ended needle cannula to the distal end of the vial holder such that the proximal point of the needle cannula pierces the elastomeric seal on the vial. The patient then selects a dose and operates the pen to urge the plunger distally to deliver the selected dose. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above.

The above described reusable medication delivery pen is effective and much more convenient for self-administration of medication than the hypodermic syringes using separate medication vials. However, the move to reduce the size of medication delivery pens has caused similar reduction in the size of dosage numerals used to set the desired dose on such pens. As a result, users with impaired vision have found it difficult to readily set the dose on such pens. Since it is particularly common among patients with diabetes to have complications of the disease causing impaired vision even more of a need has been found to address this problem. Some medication delivery pens have been made with limited magnification of the dosage numerals but the technique currently being used to magnify the dosage numerals leads to a medication delivery pen having an unacceptably large diameter or insufficient magnification. Hence, it is necessary to provides a medication delivery pen having integral magnification of the dosage numerals that provide sufficient magnification without adding an unacceptable increase in the diameter of the medication delivery pen or unnecessary bulk.

SUMMARY OF THE INVENTION

The present invention relates to a medication delivery pen that addresses the above-identified problem by incorporating means for magnification into the pocket clip of the medication delivery pen so that the pocket clip both provides means for magnifying the dosage numerals and functions as a clip for retaining the medication delivery pen in a user's shirt pocket. The present invention provides an improvement in user visibility of the dosage numerals since the magnification enlarges the image of each digit or font character of the dosage numeral and aides the vision of the user. The magnifying means is integrated into the pocket clip of the medication delivery pen such that the dosage numerals below the magnification means are sufficiently magnified.

Alternatively, if dosage numerals are displayed in multiple positions within the dosage display window on the medication delivery pen the entire clip can be made as a magnifier to provide magnification of a dosage numeral anywhere within the dosage display window. That embodiment provides an increase in magnification throughout the whole magnifier clip such that the digit found below the magnifier clip does not need to be stationery within the dosage display window of the medication delivery pen and is therefore free to move longitudinally, axially or rotationally and still be magnified by the magnifier pocket clip.

BRIEF DESCRIPTION OF THE DRAWINGS

FIG. 5 is a perspective view of yet another medication pen having an alternative pocket clip magnifier according to the present invention.

DETAILED DESCRIPTION OF THE INVENTION

Figure 1:
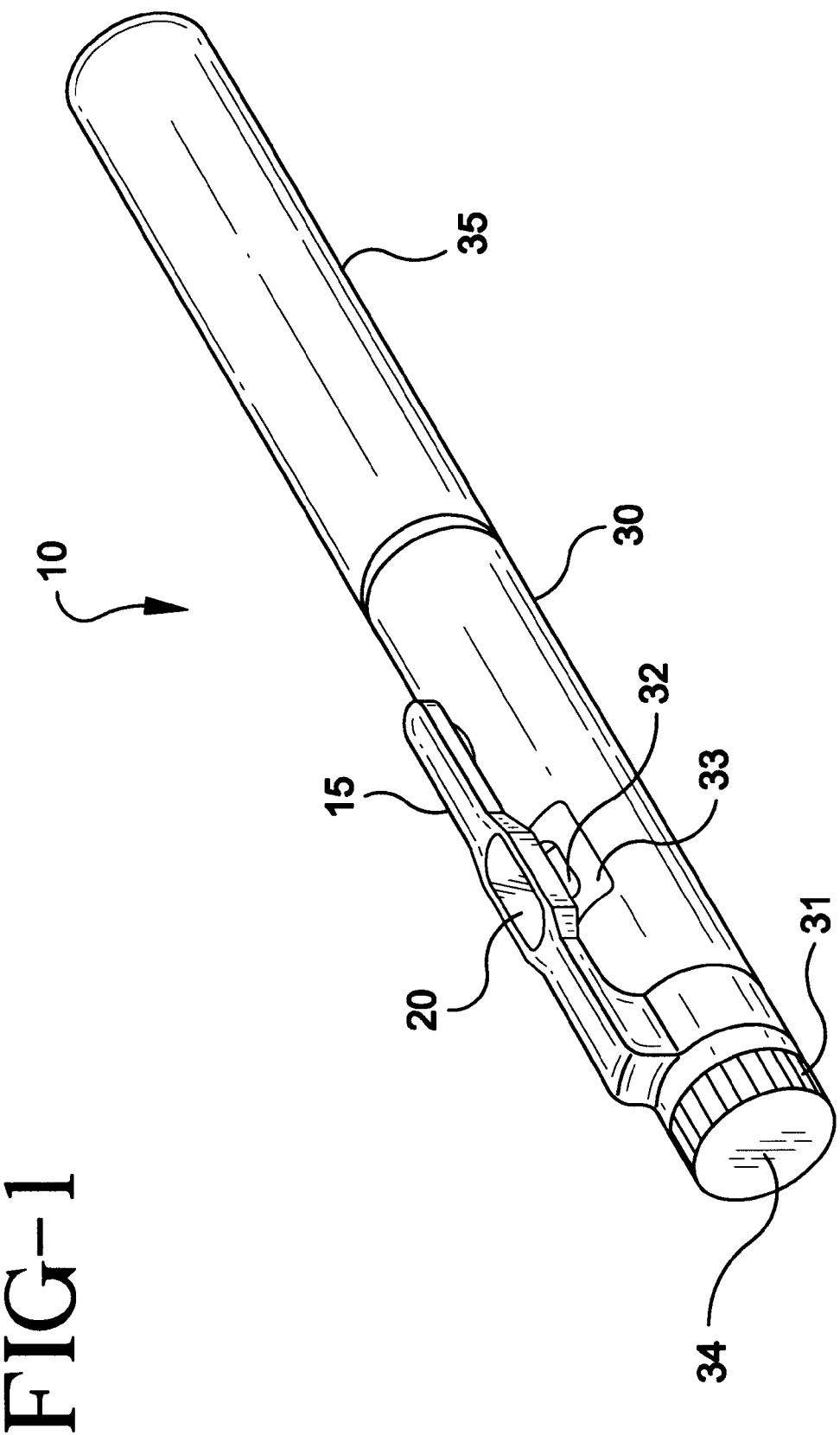
FIG. 1 is a perspective view of a medication delivery pen having a magnifier in a pocket clip according to the present invention.

A medication delivery pen 10 having a pocket clip 15 including a magnifier 20 according to the present invention is shown in FIG. 1. Medication delivery pen 10 also includes a pen body assembly 30 with a shielding cap 35 removably attached thereto to cover a needle assembly (not shown) between uses of medication delivery pen 10.

Figure 3:
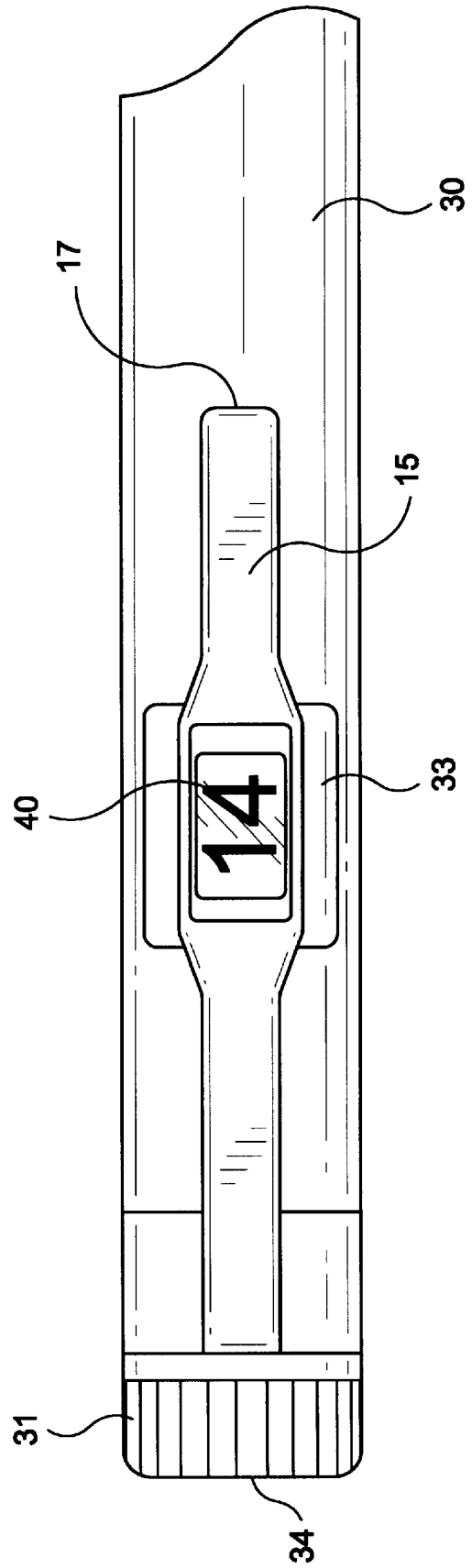
FIG. 3 is an elevational view of the magnifier in the pocket clip on the medication delivery pen shown in FIG. 1.

Pen body assembly 30 includes a dose setting dial 31 that is used to set a desired dose to be injected by the user using medication delivery pen 10. Pen body assembly 30 also includes a window insert 33 mounted thereon having a cut-out or window 32 through which the user may view dosage numerals therein. Window 32 is disposed in insert 33 on the side of pen body assembly 30 to enable dosage numerals 40 to be visible by the user through window 32 and magnifier 20 as the user is setting the dose using dose setting dial 31. Dosage numerals 40, shown in FIG. 3, are used by the user to set the dosage desired for the next injection.

Rotatable dose setting dial 31 includes a knurled exterior surface to facilitate manipulation for setting the selected dose. FIG. 1 also shows an actuator button 34 that is used by the user when performing an injection after a desired dose has been set.

Figure 2:
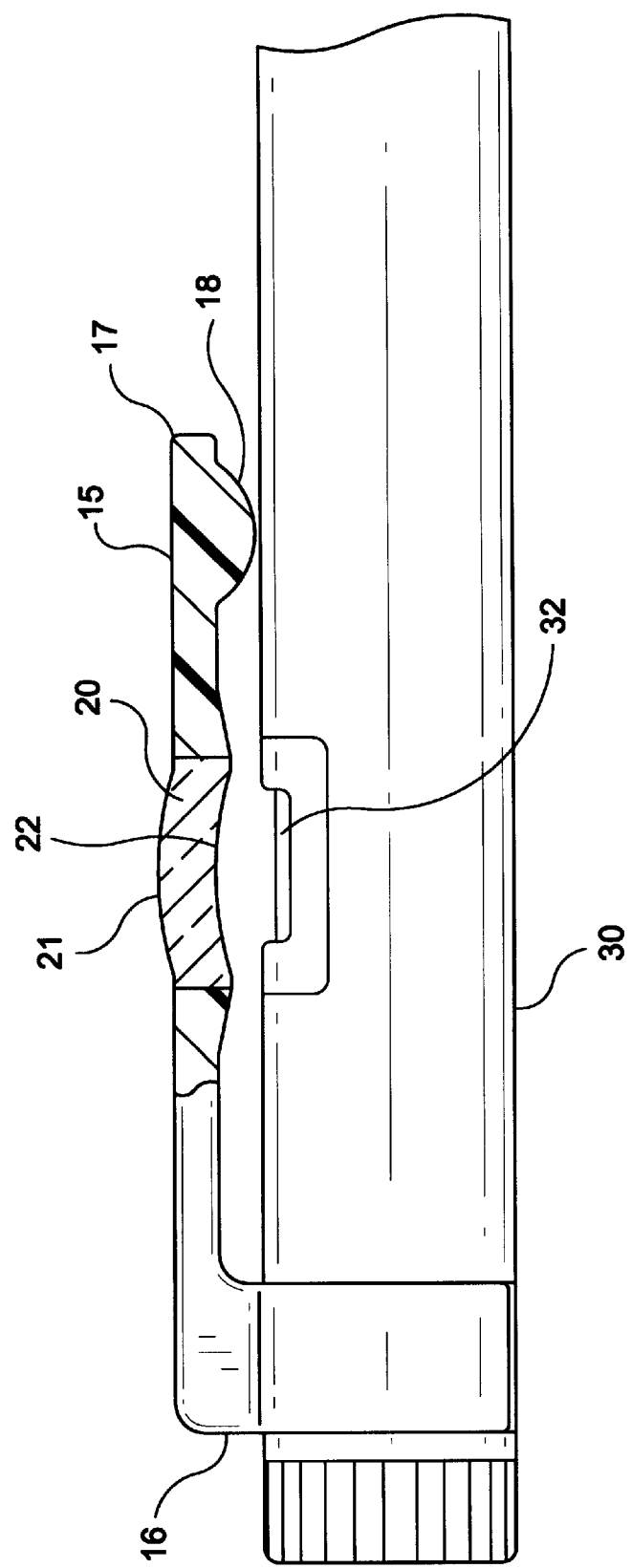
FIG. 2 is a cross-sectional view of the magnifier in the pocket clip on the medication delivery pen shown in FIG. 1.

FIG. 2 shows a cross-sectional view of pocket clip 15 including magnifier 20. Pocket clip 15 is attached to pen body assembly 30 by extension 16 and extends in a distal direction to a distal end 17 having a foot 18 in pressure contact with or close proximity to the surface of pen body assembly 30. Magnifier 20, shown in FIG. 2, has an upper convex surface 21 and a lower concave or flat surface 22 that is positioned directly over window 32 at a predetermined distance to sufficiently magnify dosage numeral 40 within window 32. As shown in FIG. 3, when magnified by magnifier 20 dosage numerals 40 are sufficiently enlarged so that a user can easily read the numerals while setting a dose using dose setting dial 31.

Figure 4:
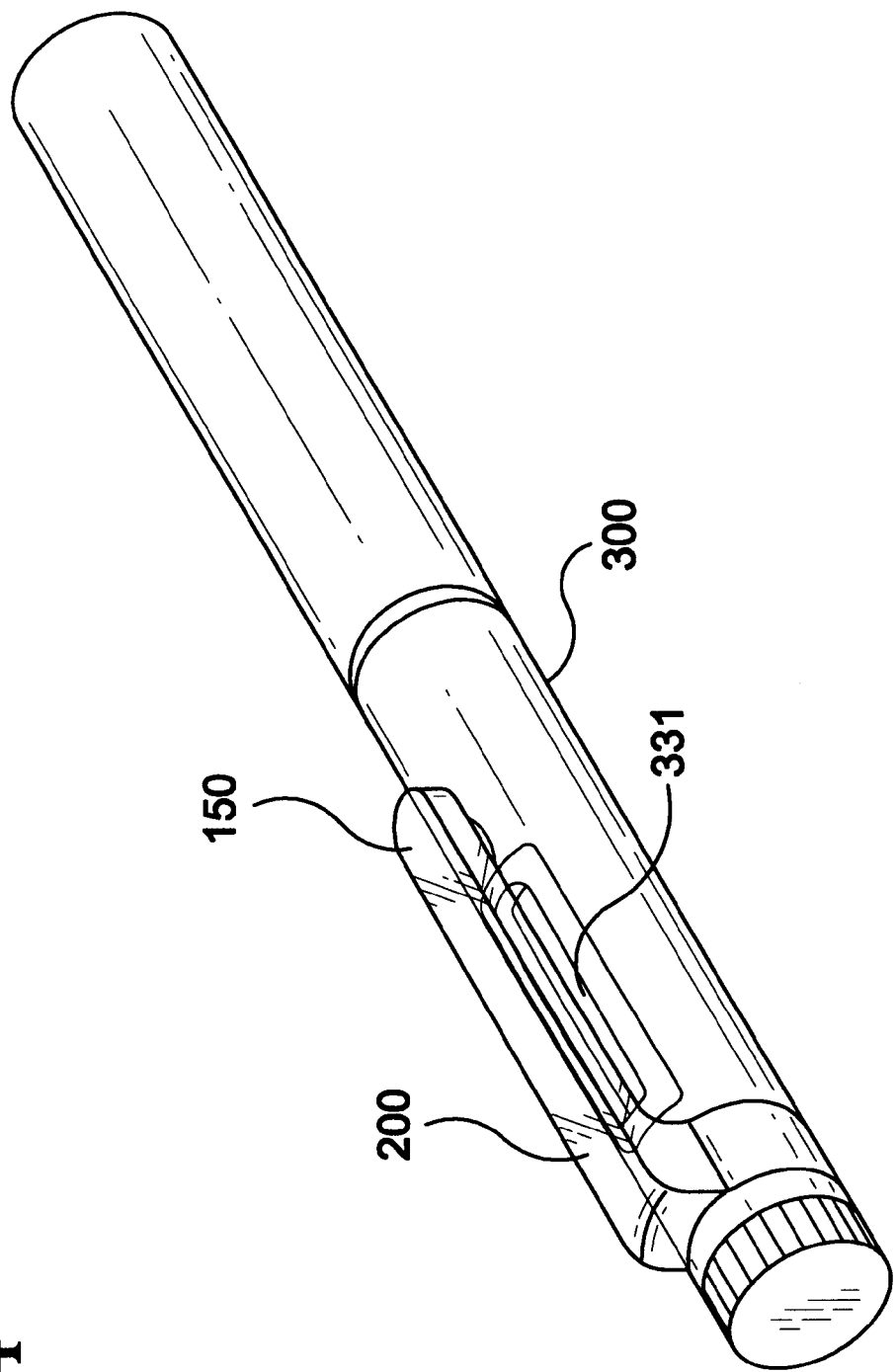
FIG. 4 is a perspective view of another medication pen having an alternative pocket clip magnifier according to the present invention.

An alternative embodiment is shown in FIG. 4 having a pocket clip 150 that extends over a longitudinally extending window 331 in pen housing 300. Pocket clip 150 includes a magnifying window 200 that extends the full length of window 331 so that if dosage numerals 40 appear anywhere within window 331 they will be properly magnified so to be easily seen and read by a user while setting a dose with medication delivery pen 10.

Another embodiment of a medication delivery pen according to the present invention is shown in FIG. 5 having a rotatable pocket clip 415 that extends over a rotatable display band 433 located on a pen housing 430. Display band 433 includes a window 432 for displaying the currently set dose. As a dose is being set and/or delivered, rotatable display band 433 rotates which causes window 432 to rotate about pen housing 430. In this embodiement pocket clip 415 is attached to pen housing 430 by an arm 416 that allows pocket clip 415 to rotate about pen housing 430. Pocket clip 415 is rotated about pen housing 430 until a magnifying window 420 on pocket clip 415 is positioned over window 432 so that the dosage therein is magnified so to be easily seen and read by a user setting a dose with the medication delivery pen. Alternatively, pocket clip 415 can rotate with window 432 during dose setting so that magnifying window 420 is always positioned over window 432.

While the present invention has been described with respect to a preferred and an alternative embodiment, it is apparent that various changes can be made without departing from the scope of the invention as defined by the appended claims.

What is claimed is:

1. A medication delivery pen comprising:

a housing having a dose display window for displaying a dose, said dose display window being rotatable about said housing; and a pocket clip on said housing extending over the dose display window and including a magnifying section to magnify the dose displayed in the dose display window, said pocket clip being rotatable about said housing.

2. A medication delivery pen according to claim 1, wherein the dose display window extends in a longitudinal direction and displays the dose anywhere therein, and wherein the magnifying section extends over the entire length of said window to magnify the dose displayed therein.

3. A medication delivery pen according to claim 1, wherein the magnifying section extends over and beyond said window to magnify the dose displayed in said window.

4. A medication delivery pen according to claim 1, wherein the dose display window and the pocket clip are rotatably mounted to said housing to rotate in conjunction.

5. A medication delivery pen comprising:

a housing having means for setting a desired dose and means for displaying the desired dose set by the dose setting means, said display means including a window rotatable about said housing for displaying the desired dose;

a pocket clip on said housing extending over said dose display means; and means mounted on said pocket clip for magnifying the desired dose displayed by said dose display means, wherein said pocket clip is rotatable about said housing such that said magnifying means magnifies the desired dose displayed in said window.

6. A medication delivery pen according to claim 5, wherein said window extends in a longitudinal direction and displays the desired dose anywhere therein, and wherein said magnifying means magnifies said window to magnify the desired dose displayed anywhere therein.

7. A medication delivery pen according to claim 6, wherein said magnifying means extends over and beyond said window.

* * * * *